(12) United States Patent
Hillbratt et al.

(10) Patent No.: US 10,455,334 B2
(45) Date of Patent: Oct. 22, 2019

(54) SIGNAL AMPLIFIER (71) Applicant: Cochlear Limited, Macquarie University, NSW (AU)

(72) Inventors: Martin Evert Gustaf Hillbratt, Mölnlycke (SE); Rune Stefan Oscarsson, Stora Höga (SE); Sören Ingemar Nilsson, Mölnlycke (SE)

(73) Assignee: Cochlear Limited, Macquarie University, NSW (AU)

( * ) Notice: Subject to any disclaimer, the term of this patent is extended or adjusted under 35 U.S.C. 154(b) by 0 days.

(21) Appl. No.: 15/791,706

(22) Filed: Oct. 24, 2017

(65) Prior Publication Data
US 2018/0048967 A1 Feb. 15, 2018

Related U.S. Application Data (63) Continuation of application No. 14/835,716, filed on Aug. 26, 2015, now abandoned.
(Continued)

(51) Int. Cl.
*H04R 25/00* (2006.01)
*H03F 3/21* (2006.01)
(Continued)

(52) U.S. Cl.
CPC ......... *H04R 25/505* (2013.01); *A61N 1/0541* (2013.01); *A61N 1/08* (2013.01); *A61N 1/36036* (2017.08); *H03F 1/34* (2013.01); *H03F 3/187* (2013.01); *H03F 3/211* (2013.01); *H03F 3/2173* (2013.01); *H03F 2200/03* (2013.01); *H03F 2200/429* (2013.01); *H04R 2225/59* (2013.01); *H04R 2225/61* (2013.01)

(58) Field of Classification Search
CPC .............. H04R 25/505; H04R 2225/59; H04R 2225/61; H03F 3/187; H03F 3/68; H03F 3/211; H03F 3/2173; H03F 2200/03; H03F 2200/429
See application file for complete search history.

(56) References Cited

U.S. PATENT DOCUMENTS

5,600,728 A 2/1997 Satre
5,689,819 A 11/1997 Nishimura et al.
(Continued)

*Primary Examiner* — Sunita Joshi
(74) *Attorney, Agent, or Firm* — Edell, Shapiro & Finnan, LLC (57) ABSTRACT

A hearing prosthesis circuit includes a power source, a first amplifier coupled to the power source, and a second amplifier coupled to the power source. The circuit also includes a stimulation component coupled to the first amplifier and the second amplifier. The stimulation component is configured to provide an output in accordance with an electrical signal that includes audio data. Further, the circuit includes a controller coupled to the first amplifier and the second amplifier. The controller is operable in accordance with a first operational setting to use the first amplifier to provide the electrical signal to the stimulation component and the controller is also operable in accordance with a second operational setting to use the second amplifier to provide the electrical signal to the stimulation component. Generally, the first amplifier provides greater signal amplification of the audio data than the second amplifier.

21 Claims, 9 Drawing Sheets

Related U.S. Application Data

(60) Provisional application No. 62/082,117, filed on Nov. 19, 2014.

(51) Int. Cl.
  *H03F 1/34* (2006.01)
  *H03F 3/187* (2006.01)
  *A61N 1/08* (2006.01)
  *H03F 3/217* (2006.01)
  *A61N 1/05* (2006.01)
  *A61N 1/36* (2006.01)

(56) References Cited

U.S. PATENT DOCUMENTS

| | | | | |
|---|---|---|---|---|
| 7,321,262 | B2 | 1/2008 | Nielsen et al. | |
| 2008/0123881 | A1* | 5/2008 | Alexander | H03F 3/187 |
| | | | | 381/312 |
| 2010/0027820 | A1* | 2/2010 | Kates | G10L 25/00 |
| | | | | 381/312 |
| 2011/0216929 | A1* | 9/2011 | Jang | H04R 25/00 |
| | | | | 381/321 |
| 2015/0045095 | A1* | 2/2015 | D'Souza | H03F 3/187 |
| | | | | 455/572 |

\* cited by examiner

SIGNAL AMPLIFIER

CROSS-REFERENCE TO RELATED APPLICATION

This application is a continuation application of U.S. patent application Ser. No. 14/835,716, entitled "Signal Amplifier", filed on Aug. 26, 2015, which in turn claims priority to U.S. Provisional Application No. 62/082,117, entitled "Signal Amplifier", filed Nov. 19, 2014 (expired). The content of these applications are hereby incorporated by reference herein.

BACKGROUND

Various types of hearing prostheses provide persons with different types of hearing loss with the ability to perceive sound. Hearing loss may be conductive, sensorineural, or some combination of both conductive and sensorineural. Conductive hearing loss typically results from a dysfunction in any of the mechanisms that ordinarily conduct sound waves through the outer ear, the eardrum, and/or the bones of the middle ear. Sensorineural hearing loss typically results from a dysfunction in the inner ear, such as in the cochlea where sound or acoustic vibrations are converted into neural signals, or any other part of the ear, auditory nerve, or brain that may process the neural signals.

Persons with some forms of conductive hearing loss may benefit from hearing prostheses, such as acoustic hearing aids or vibration-based hearing devices. An acoustic hearing aid typically includes a small microphone to detect sound, an amplifier to amplify certain portions of the detected sound, and a small speaker to transmit the amplified sound into the person's ear. Vibration-based hearing devices typically include a small microphone to detect sound and a vibration mechanism to apply vibrations, which represent the detected sound, directly or indirectly to a person's bone or teeth, thereby causing vibrations in the person's inner ear and bypassing the person's auditory canal and middle ear.

Vibration-based hearing devices include, for example, bone conduction devices, direct acoustic cochlear stimulation devices, and other vibration-based devices. A bone conduction device typically utilizes a surgically implanted mechanism or a passive connection through the skin or teeth to transmit vibrations via the skull. Similarly, a direct acoustic cochlear stimulation device typically utilizes a surgically implanted mechanism to transmit vibrations, but bypasses the skull and more directly stimulates the inner ear. Other vibration-based hearing devices may use similar vibration mechanisms to transmit acoustic signals via direct or indirect vibration applied to teeth or other cranial or facial structures.

Persons with certain forms of sensorineural hearing loss may benefit from implanted prostheses, such as cochlear implants and/or auditory brainstem implants. Generally, cochlear implants and auditory brainstem implants electrically stimulate auditory nerves in the cochlea or the brainstem to enable persons with sensorineural hearing loss to perceive sound. For example, a cochlear implant uses a small microphone to convert sound into a series of electrical signals, and uses the series of electrical signals to stimulate the auditory nerve of the recipient via an array of electrodes implanted in the cochlea. An auditory brainstem implant can use technology similar to cochlear implants, but instead of applying electrical stimulation to a person's cochlea, the auditory brainstem implant applies electrical stimulation directly to a person's brainstem, bypassing the cochlea altogether.

In addition, some persons may benefit from a bimodal hearing prosthesis that combines one or more characteristics of acoustic hearing aids, vibration-based hearing devices, cochlear implants, or auditory brainstem implants to enable the person to perceive sound.

SUMMARY

A hearing prosthesis may include an output amplifier stage to boost or amplify an electrical signal applied to stimulation electronics (which may include a speaker, a vibration actuator, cochlear electrodes, and the like) and, thus, to amplify an output of the stimulation electronics. In one example, the present disclosure is directed to an output amplifier stage or circuit that includes a first amplifier (e.g., a step-up converter coupled to a power source and including charge storage circuitry and switching circuitry). The output amplifier stage may also include a second amplifier (e.g., a class-D amplifier coupled to a power source and including switching circuitry).

The present disclosure also relates to a controller or control circuitry coupled to the first and second amplifiers. In one example, the controller is operable in accordance with different operational settings or modes to selectively use the first or second amplifiers to provide an electrical stimulation signal to a stimulation component. For instance, the controller may operate in a first mode that uses the first amplifier (e.g., for providing higher amplitude signals to the stimulation component) and the controller may operate in a second mode that uses the second amplifier (e.g., for providing relatively lower amplitude signals to the stimulation component).

In a further aspect of the present disclosure, the output amplifier stage or circuit includes two or more amplifiers that may operate in parallel. For instance, the output amplifier stage includes at least a first amplifier that is configured to amplify portions of an input signal that are below a threshold or cutoff frequency, and a second amplifier that is configured to amplify portions of the input signal that are above the threshold or cutoff frequency. In this example, the first amplifier is configured to generate an output signal with a relatively higher current but with a relatively lower voltage, and the second amplifier is configured to generate an output signal with a relatively lower current but with a relatively higher voltage. The output signals from the two amplifiers are then combined or otherwise applied to a load (e.g., the stimulation component). In this aspect, the first and second amplifiers may be coupled to different power sources. For example, a low impedance, low voltage power source may be coupled to the first amplifier, and a step-up voltage converter may be coupled to the second amplifier.

In another aspect, the present disclosure is directed to a hearing prosthesis circuit that includes a first amplifier coupled in series with a second amplifier. In this aspect, a load is coupled to receive an output signal from the second amplifier, wherein an impedance of the load is dependent on a frequency of the output signal. The circuit further includes a controller coupled to the first amplifier. The controller may be configured to limit a power output of the first amplifier for a discrete set of one or more frequencies that correspond to the impedance of the load being above a predetermined threshold. In another example, the controller is configured to limit the power output of the first amplifier differently depending on whether a wireless audio streaming function is in use or not.

DETAILED DESCRIPTION

The following detailed description sets forth various features and functions of the disclosed embodiments with reference to the accompanying figures. In the figures, similar reference numbers typically identify similar components, unless context dictates otherwise. The illustrative embodiments described herein are not meant to be limiting. Aspects of the disclosed embodiments can be arranged and combined in a variety of different configurations, all of which are contemplated by the present disclosure. For illustration purposes, some features and functions are described with respect to medical devices, such as hearing prostheses. However, the features and functions disclosed herein may also be applicable to other types of devices, including other types of medical and non-medical devices.

Overview

The present disclosure relates to an output stage or circuit configured to amplify electrical signals. The output stage disclosed herein may be incorporated in a variety of electrical components, devices, and systems, and may also be used to implement processes or methods for amplifying electrical signals. In an example, the output stage is configured to amplify an electrical signal, which may include audio data, such that stimulation electronics or components of a hearing prosthesis can apply a corresponding amplified output signal that a recipient or user of the hearing prosthesis may perceive as sound.

Generally, various considerations may be relevant to the design and use of an output amplifier stage, such as power efficiency, quiescent power consumption, power supply characteristics, input and output signal levels, device impedance characteristics, and hearing prosthesis user programs or maps, among others. In one example, an output stage disclosed herein includes a combined step-up converter and class-D amplifier that is characterized by greater efficiency and lower quiescent power consumption than a separate step-up converter and a separate class-D amplifier. Further, the combined step-up converter and class-D amplifier may also provide the benefit of a more compact configuration than a separate step-up converter and separate class-D amplifier.

In another example, an output stage disclosed herein includes parallel amplifiers, which may include step-up converters, class-D amplifiers, and/or complied step-up converters and class-D amplifiers. The parallel amplifiers may have different supply voltages and may work in parallel to amplify different portions of an input signal. The different portions of the input signal may correspond to different frequency bands of the input signal.

In addition, the present disclosure is also directed to a controller that is configured to switch the disclosed output stage between different operating modes (and amplifiers) depending on power supply characteristics, input/output signal levels, device impedance characteristics, and hearing prosthesis user programs, for instance. Generally, as disclosed in more detail hereinafter, if a greater power output is desired, a controller can operate the output stage using the combined step-up converter and class-D amplifier, and if a lower power output is acceptable, the controller can operate the output stage using a separate class-D amplifier.

The controller may also be configured to operate different amplifiers of the disclosed output stage in parallel for different frequency ranges or bands of an input signal.

Example Electronic Device or System

Figure 1:
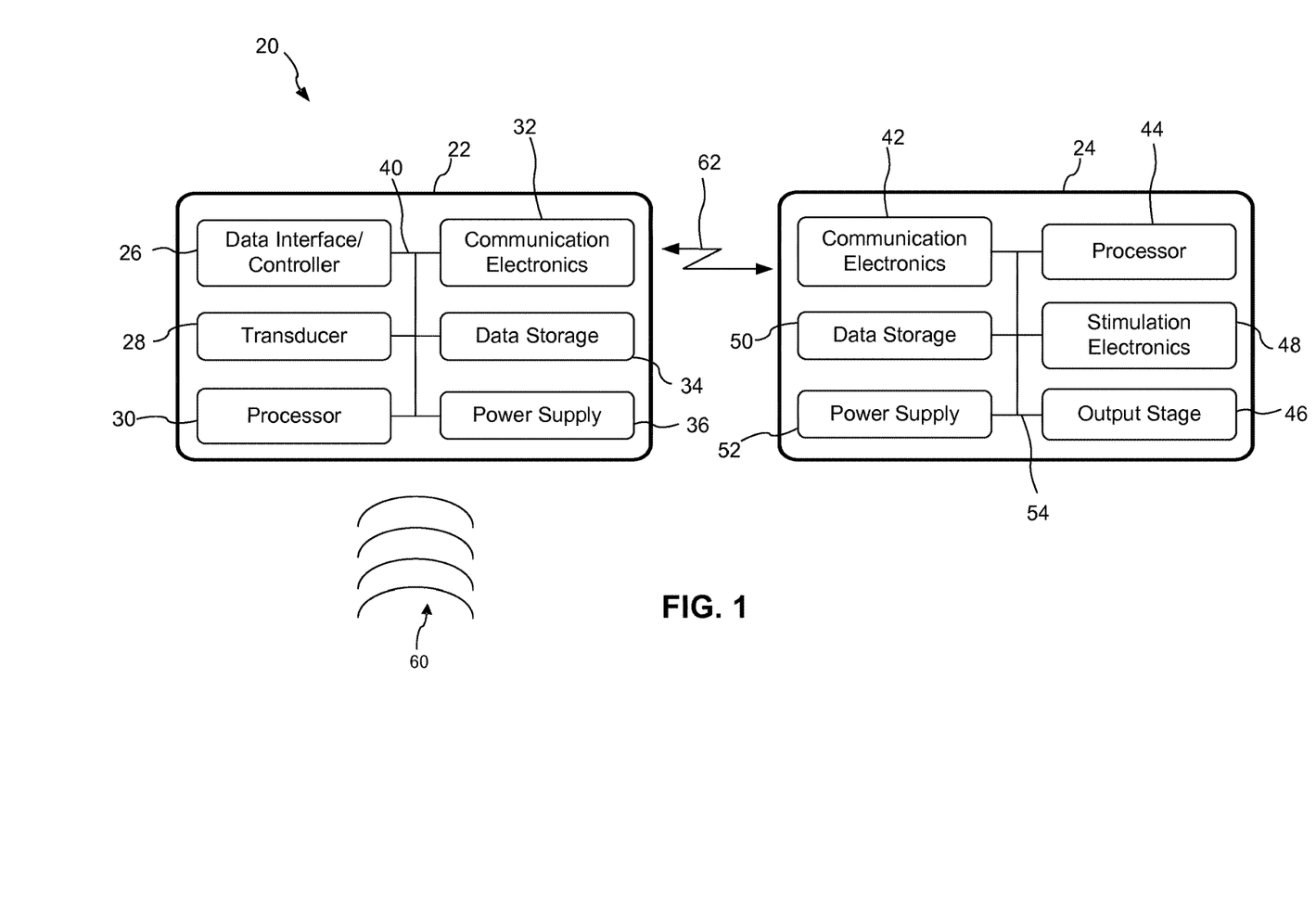
FIG. 1 is a block diagram of a device according to an embodiment of the present disclosure.

Referring now to FIG. 1, an example electronic device or system 20 includes a first component 22 and a second component 24. The device 20 can be a hearing prosthesis, such as a cochlear implant, an acoustic hearing aid, a bone conduction device, a direct acoustic cochlear stimulation device, an auditory brainstem implant, a bimodal hearing prosthesis, a middle ear stimulating device, or any other type of hearing prosthesis configured to assist a prosthesis recipient to perceive sound. In this context, the first component 22 can be generally external to a recipient and communicate with the second component 24, which can be implanted in the recipient. In other examples, the components 22, 24 can both be at least partially implanted or can both be at least partially external to the recipient. In yet other examples, the first and second component 22, 24 may be combined into a single operational component or device. In such examples, the single unit (i.e., combined first component 22 and second component 24) may be totally implanted. Generally, an implantable component or device can be hermetically sealed and otherwise adapted to be at least partially implanted in a person.

In FIG. 1, the first component 22 includes a data interface 26 (such as a universal serial bus (USB) controller), one or more transducers 28, a processor or controller 30 (such as a digital signal processor (DSP)), communication electronics 32 (such as an electromagnetic radio frequency (RF) transceiver), data storage 34, and a power supply 36, all of which may be coupled directly or indirectly via a wired conductor or wireless link 40. In the example of FIG. 1, the second component 24 includes communication electronics 42 (such as another RF transceiver), a processor or controller 44, an output amplifier stage or circuit 46, stimulation electronics 48, data storage 50, and a power supply 52, all of which may be coupled directly or indirectly via a wired conductor or wireless link 54.

The transducer 28 may include a microphone that is configured to receive external audible sounds 60. Further, the microphone may include combinations of one or more omnidirectional or directional microphones configured to receive background sounds and/or to focus on sounds from a specific direction, such as generally in front of the prosthesis recipient. Alternatively or in addition, the transducer 28 may include telecoils or other sound transducing components that receive sound and convert the received sound to electronic signals. Further, the device 20 may be configured to receive sound information from other sound input sources, such as electronic sound information received through the data interface 26.

In one example, the processor 30 of the first component 22 is configured to convert or encode the audible sounds 60 (or other electronic sound information) into encoded electronic signals that include audio data representing sound information, and to apply the encoded electronic signals to the communication electronics 32. In the present example, the communication electronics 32 of the first component 22 are configured to transmit the encoded electronic signals as electronic output signals 62 to the communication electronics 42 of the second component 24. Illustratively, the communication electronics 32, 42 can include magnetically coupled coils that establish an RF link between the units 22, 24. Accordingly, the communication electronics 32 can transmit the output signals 62 encoded in a varying or alternating magnetic field over the RF link between the components 22, 24.

The processor 44 is configured to decode the received output signals 62 and extract the encoded electronic signals. The second component 24 can then apply the encoded electronic signals to the output stage 46, which is configured to amplify the encoded electronic signals, as needed, and apply the amplified electronic signals to the stimulation electronics 48. The stimulation electronics 48 use the applied amplified electronic signals to generate an output that allows a recipient to perceive the electronic signals as sound. Generally, the stimulation electronics 48 can include a transducer or actuator that provides auditory stimulation to the recipient through one or more of electrical nerve stimulation, audible sound production, or mechanical vibration of the cochlea, for example.

Each of the power supplies 36, 52 provides power to various components of the first and second components 22, 24, respectively. In another variation of the system 20 of FIG. 1, one of the power supplies may be omitted, for example, the system may include only the power supply 36 or the power supply 52, which is used to provide power to other components. The power supplies 36, 52 can be any suitable power supply, such as one or more non-rechargeable or rechargeable batteries. In one example, one or more of the power supplies 36, 52 are batteries that can be recharged wirelessly, such as through inductive charging. Generally, a wirelessly rechargeable battery facilitates complete subcutaneous implantation of a device to provide a fully or at least partially implantable prosthesis. A fully implanted hearing prosthesis has the added benefit of enabling the recipient to engage in activities that expose the recipient to water or high atmospheric moisture, such as swimming, showering, saunaing, etc., without the need to remove, disable or protect, such as with a water/moisture proof covering or shield, the hearing prosthesis.

A fully implanted hearing prosthesis also spares the recipient of stigma, imagined or otherwise, associated with use of the prosthesis.

Further, the data storage 34, 50 may be any suitable volatile and/or non-volatile storage components. The data storage 34, 50 may store computer-readable program instructions and perhaps additional data. In some embodiments, the data storage 34, 50 stores data and instructions used to perform at least part of the processes disclosed herein and/or at least part of the functionality of the systems described herein. Although the data storage 34, 50 in FIG. 1 are illustrated as separate blocks, in some embodiments, the data storage can be incorporated, for example, into the processor(s) 30, 44, respectively.

Various modifications can be made to the device 20 illustrated in FIG. 1. For example, a user interface or input/output devices can be incorporated into the first component 22 and/or the second component 24. In another example, the second component 24 can include one or more microphones. Generally, the device 20 may include additional or fewer components arranged in any suitable manner. In some examples, the device 20 may include other components to process external audio signals, such as components that measure vibrations in the skull caused by audio signals and/or components that measure electrical outputs of portions of a person's hearing system in response to audio signals.

Example Output Amplifier Stages and Operation

Figure 2:
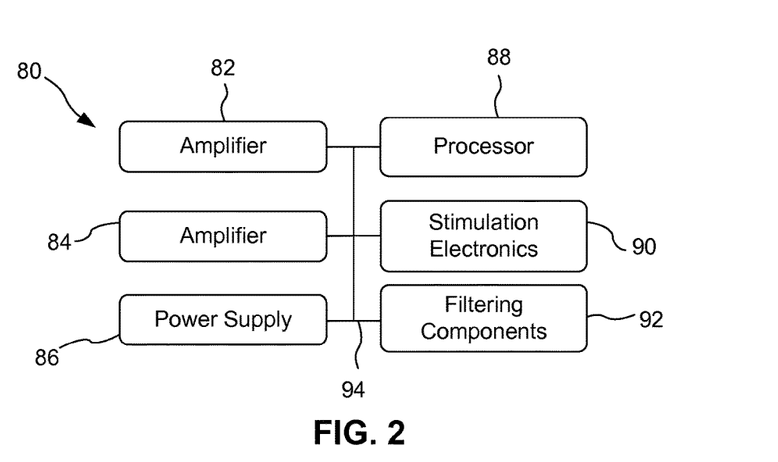
FIG. 2 is a block diagram of an output amplifier stage according to an embodiment of the present disclosure.

Referring now to FIG. 2, a block diagram of an example amplifier circuit 80 is shown, which can be an implementation of the output stage 46 of FIG. 1. The illustrated circuit 80 includes a first amplifier 82, a second amplifier 84, and a power supply 86. The power supply 86 can be the same as the power supply 52 of FIG. 1. The circuit 80 also includes a processor 88 and stimulation electronics 90, which can be the same as the processor 44 and the stimulation electronics 48, respectively, of FIG. 1. In addition, the illustrated circuit 80 includes filtering components 92. The filtering components 92 are generally used to control interference that may be caused by capacitive, resistive, and/or inductive components of the stimulation electronics and/or the output stage. In order to control the interference, the filtering components may be coupled in a feedback loop with the stimulation electronics 90. The processor 88 may also include other filtering components or functions. Some or all of the components of FIG. 2 may be coupled directly or indirectly via a wired conductor or wireless link 94.

Figure 3:
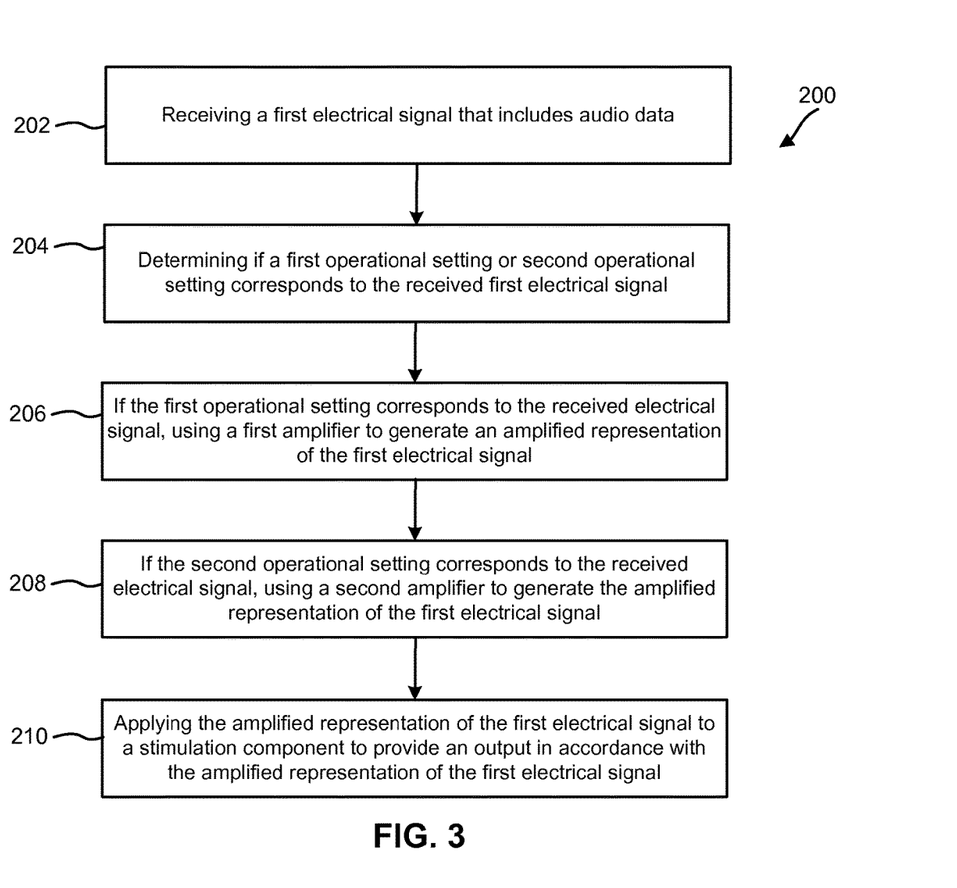
FIG. 3 is a flowchart showing a method for operating an output amplifier stage in accordance with an embodiment of the present disclosure.

Referring now to FIG. 3 and with further reference to the description above, one example method 200 is illustrated for operating the circuit 80 of FIG. 2. Generally, the method 200 may include one or more operations, functions, or actions as illustrated by one or more of blocks 202-210. Although the blocks 202-210 are illustrated in sequential order, these blocks may also generally be performed concurrently and/or in a different order than illustrated. The method 200 may also include additional or fewer blocks, as needed or desired. For example, the various blocks 202-210 can be combined into fewer blocks, divided into additional blocks, and/or removed based upon a desired implementation.

The method 200 can be performed using the device 20 and the circuit 80 described above, for example, or some other device or circuit, such as the circuits described hereinafter. In the method 200, at block 202, the processor 88, for example, receives a first electrical signal that includes audio data. At block 204, the processor 88 determines if a first operational setting or second operational setting corresponds to the received first electrical signal. If the first operational setting corresponds to the first electrical signal, at block 206, the processor 88 uses a first amplifier (e.g., the amplifier 82 of FIG. 2) to generate an amplified representation of the first electrical signal. If the second operational setting corresponds to the first electrical signal, at block 208, the processor 88 uses a second amplifier (e.g., the amplifier 84 of FIG. 2) to generate an amplified representation of the first electrical signal. Generally, using the first amplifier provides greater amplification of the first electrical signal than using the second amplifier. Thereafter, at block 210, the circuit 80 applies the amplified representation of the first electrical signal to a stimulation component (e.g., the stimulation electronics 90 of FIG. 2) for providing an output in accordance with the amplified representation of the first electrical signal. In one example, the output may be perceived as sound by a user.

In the method 200, the processor 88 may dynamically switch, based on if the first operational setting or the second operational setting corresponds to the received electrical signal, between using the first amplifier to generate the amplified representation of the first electrical signal or using the second amplifier to generate the amplified representation of the first electrical signal, respectively. Further, in one embodiment, the first amplifier includes a step-up converter and the second amplifier includes a class-D amplifier.

In various examples, the first operational setting may correspond to one or more of a music setting, a noisy environmental classification, a hearing impairment greater than a predetermined severity, or the audio data having an amplitude greater than a predetermined threshold. The second operational setting may correspond to one or more of a phone setting, a quiet environmental classification, a hearing impairment less than the predetermined severity, or the audio data having an amplitude less than the predetermined threshold, for example. Generally, the first operational setting corresponds to a higher power output requirement than the second operational setting.

In another example, the first and second operational settings correspond to higher and lower power output requirements, respectively, due to frequency-dependent device impedance characteristics. Generally, the frequency of the received electrical signal and audio data affects different types of stimulation electronics in different ways. For instance, when the stimulation electronics include an electromechanical component, such as an electromechanical vibrating actuator, the electromechanical stimulation component demonstrates lower impedance for lower frequency signals, and higher impedance for higher frequency signals. In accordance with this example of an electromechanical stimulation component, the first operational setting may correspond to received electrical signal frequencies above a predetermined frequency, such that a higher voltage signal can be applied to drive a greater output from the stimulation component. Consequently, the second operational setting may correspond to received signal frequencies below the predetermined frequency where a higher voltage signal is not needed to drive the greater power output.

In contrast, when the stimulation electronics include a piezoelectric actuator, the actuator demonstrates higher impedance for lower frequency signals, and lower impedance for higher frequency signals. In accordance with this example of a piezoelectric actuator, the first operational setting may correspond to received electrical signal frequencies below a predetermined frequency, such that a higher voltage signal can be applied to drive a greater output from the stimulation component. Accordingly, the second operational setting may correspond to received signal frequencies above the predetermined frequency.

Figure 4:
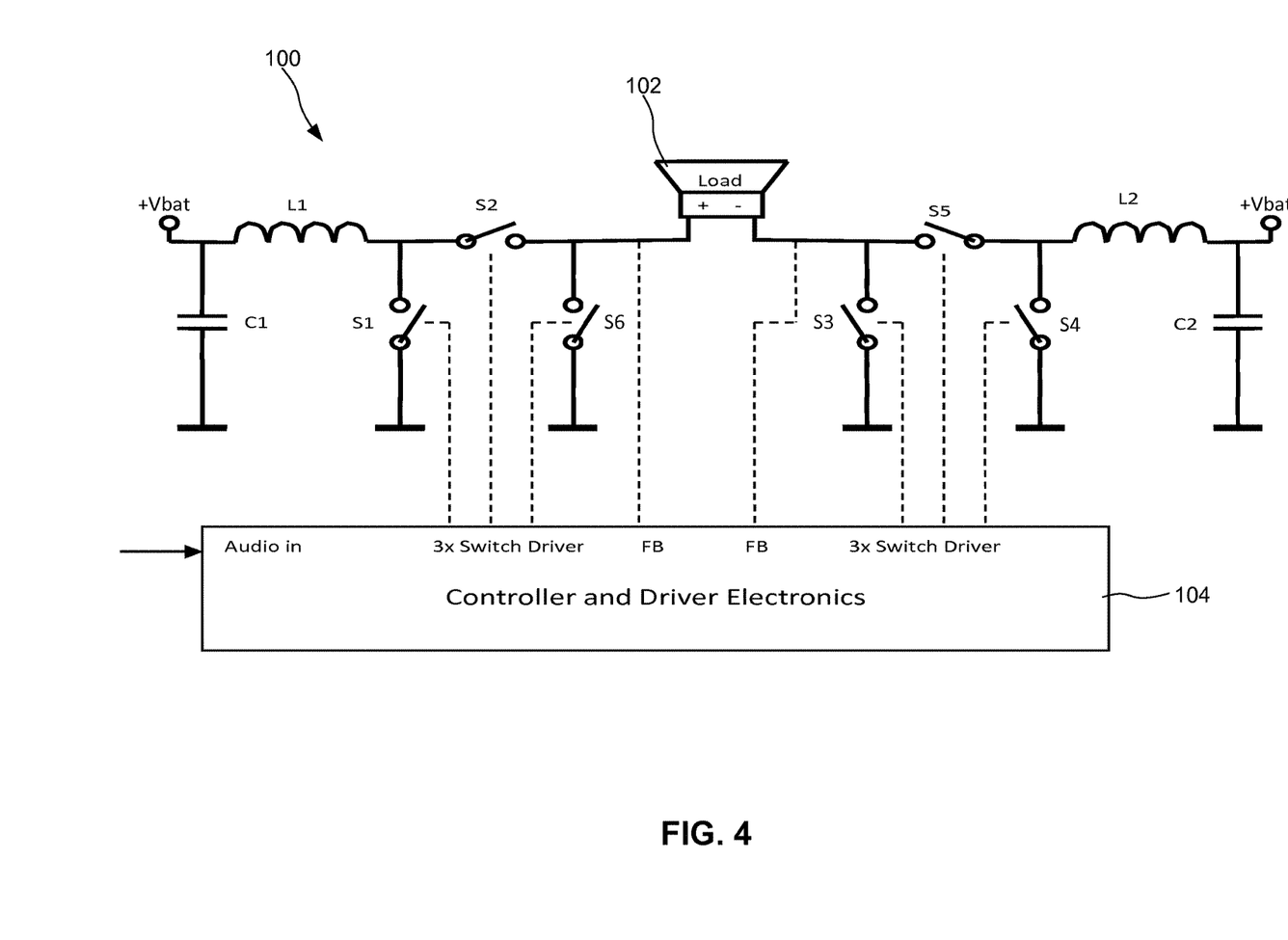
FIG. 4 is a circuit and block diagram of an output amplifier stage according to an embodiment of the present disclosure.

Referring now to FIG. 4, another example amplifier circuit or stage 100 is shown, which can form at least part of the output stage 46 of FIG. 1 and/or the amplifier circuit 80 of FIG. 2, for example. In FIG. 4, the output stage 100 includes a power supply Vbat, which can be provided by the power supply 52 of FIG. 1, for example. The output stage 100 further includes a load 102 (e.g., an actuator or transducer of the stimulation electronics 48), and a controller/driver electronics 104, which can be implemented, at least in part, by the processor 44, for example. As illustrated in FIG. 4, the controller 104 is configured to receive encoded electronic signals that include audio data (at Audio in), and to control the output stage 100 in accordance with the received encoded electronic signals to provide an amplified output to the load 102.

The amplifier circuit 100 shown in FIG. 4 includes two step-up driver stages, although, in other embodiments contemplated by the present disclosure, a single step-up driver stage can be used. The first step-up driver stage includes first charge storage circuitry, such as an inductor L1 coupled to the power source Vbat. The first output stage may also include a capacitor C1, which can function as a charge storage component and/or as a filtering component. In FIG. 4, a first terminal of the capacitor C1 is coupled to the power source Vbat and a second terminal of the capacitor C1 is coupled to ground. A first terminal of the inductor L1 is coupled to the power source Vbat and to the first terminal of the capacitor C1. A second terminal of the inductor L1 is coupled to respective first terminals of first switching circuitry S1 and second switching circuitry S2. A second terminal of the first switching circuitry S1 is further coupled to ground. A second terminal of the second switching circuitry S2 is coupled to a first terminal of the load 102 (e.g., a positive terminal of the load). A first terminal of third switching circuitry S3 is coupled to a second terminal of the load 102 and a second terminal of the third switching circuitry is coupled to ground. The switches S1, S2, S3 can be transistor switches. In one example, one or more of the switches S1-S3 may include two or more switches coupled in parallel in order to reduce switch resistance (e.g., $R_{DS}$ On/Off). In the example of FIG. 4, the first step-up driver stage includes the first charge storage circuitry (e.g., the inductor L1) and the switching circuitry S1, S2, and S3. The first step-up driver stage may also include a filtering component or other charge storage circuitry (e.g., the capacitor C1).

In the example of FIG. 4, a second step-up driver stage includes second charge storage circuitry (e.g., an inductor L2) and switching circuitry (e.g., fourth, fifth, and sixth switching circuitry S4, S5, S6, respectively). The second step-up driver may also include a filtering component or other charge storage circuitry (e.g., a capacitor C2). More particularly, in the present example, a first terminal of the capacitor C2 is coupled to the power source Vbat and a second terminal of the capacitor C2 is coupled to ground. In the illustrated example, the inductors L1, L2 and the capacitors C1, C2 are coupled to a positive pole of the power source +Vbat. In another example, the inductor L1 and the capacitor C1 may be coupled to a positive pole of the power source +Vbat, and the inductor L2 and the capacitor C2 may be coupled to a negative pole of the power source −Vbat.

In FIG. 4, a first terminal of the inductor L2 is coupled to the power source and to the first terminal of the capacitor C2. A second terminal of the inductor L2 is coupled to respective first terminals of the fourth switching circuitry S4 and the fifth switching circuitry S5. A second terminal of the fourth switching circuitry S4 is further coupled to ground. A second terminal of the fifth switching circuitry S5 is coupled to the second terminal of the load 102 (e.g., a negative terminal of the load) and to the first terminal of the third switching circuitry S3. A first terminal of the sixth switching circuitry S6 is coupled to the first terminal of the load 102, and a second terminal of the sixth switching circuitry is coupled to ground. The switches S4, S5, S6 can be transistor switches. In one example, one or more of the switches S4, S5, S6 may include two or more switches coupled in parallel in order to reduce switch resistance (e.g., $R_{CS}$ On/Off).

Figure 5:
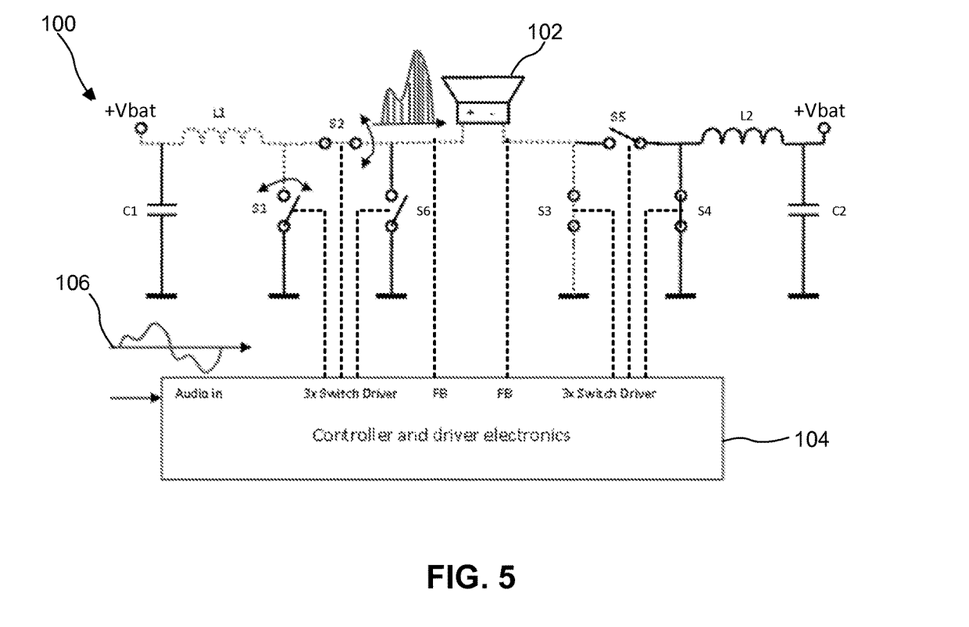
FIG. 5 is a circuit and block diagram illustrating the output amplifier stage of FIG. 4 in use, in accordance with an embodiment of the present disclosure.
Figure 6:
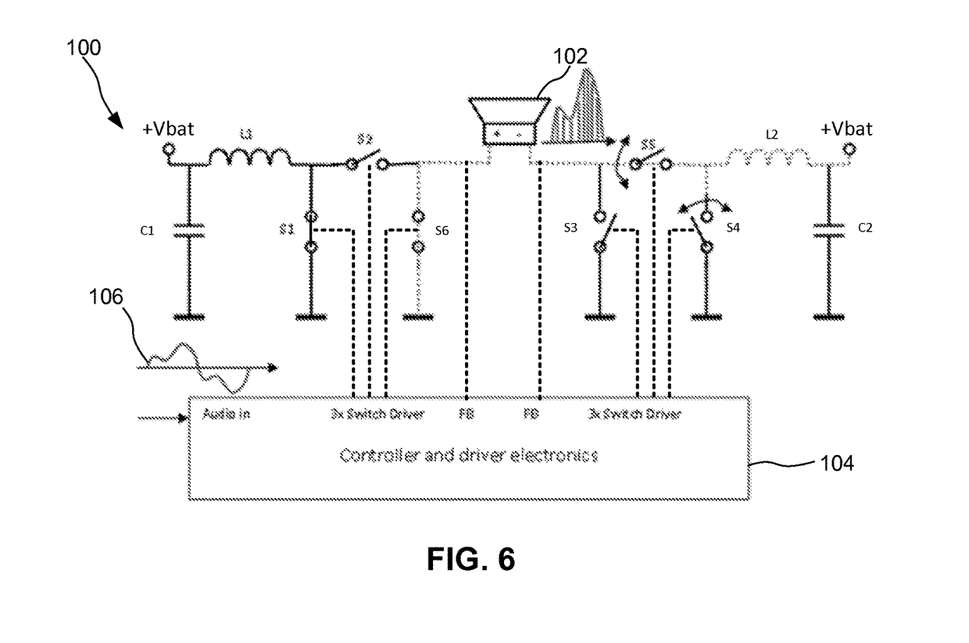
FIG. 6 is another circuit and block diagram illustrating the output amplifier stage of FIG. 4 in use, in accordance with an embodiment of the present disclosure.

An example operation of the amplifier stage is shown in FIGS. 5 and 6. In this example, during a positive half-period of an encoded audio signal 106, the controller 104 closes the third switching circuitry S3, closes the fourth switching circuitry S4, and opens the fifth switching circuitry S5, as shown in FIG. 5. In this example, closing the fourth switching circuitry S4 and opening the fifth switching circuitry S5 allows the inductor L2 to store charge from the power source, which, together with the power source Vbat, may be used to provide a stepped-up or amplified output signal to the load 102. Further, the controller actuates the first switching circuitry S1 and the second switching circuitry S2 in an opposite or inverse relation to each other. More particularly, the controller actuates the first and second switching circuitry S1, S2 in accordance with a ratio between an on-time and off-time to deliver a replica or amplified representation of the audio signal 106 at the positive pole of the load 102. The amplification of the audio signal is provided, at least in part, by the combined power from the power source and the charge stored in the inductor L1.

For a negative half-period, as seen in FIG. 6, the controller 104 closes the sixth switching circuitry S6, closes the first switching circuitry S1, and opens the second switching circuitry S2, as shown in FIG. 6. In this example, closing the first switching circuitry S41 and opening the second switching circuitry S2 allows the inductor L1 to store charge from the power source, which, together with the power source Vbat, may be used to provide a stepped-up or amplified output signal to the load 102, as discussed above in relation to FIG. 5. Further, the controller actuates the fourth switching circuitry S4 and the fifth switching circuitry S5 to deliver a replica of the audio signal 106 at the negative pole of the load 102. The controller 104 can actuate the switching circuitry pairs S4, S5 and S1, S2 to deliver a replica of the audio signal 106 using pulse width modulation or pulse density modulation, for example.

In this example, each of the first and second step-up driver output stages may be considered to be a combined step-up converter and class-D amplifier. More particularly, these output stages include step-up components (e.g., charge storage circuitry, such as inductors and/or capacitors) that, together with the power supply Vbat, directly provide a stepped-up power supply to switching components that are switched on and off as a class-D amplifier. In this case, the resulting output signal applied to the load 102 is an amplified representation of the audio signal 106.

In another example, the output amplifier stage 100 may include or otherwise be operated with only the first step-up driver stage. In a further example, additional protection circuits, such as Snubber circuits or TVS diodes, may be included in the output stage 100 to help to avoid high voltage peaks that may be caused by the inductors.

Figure 7:
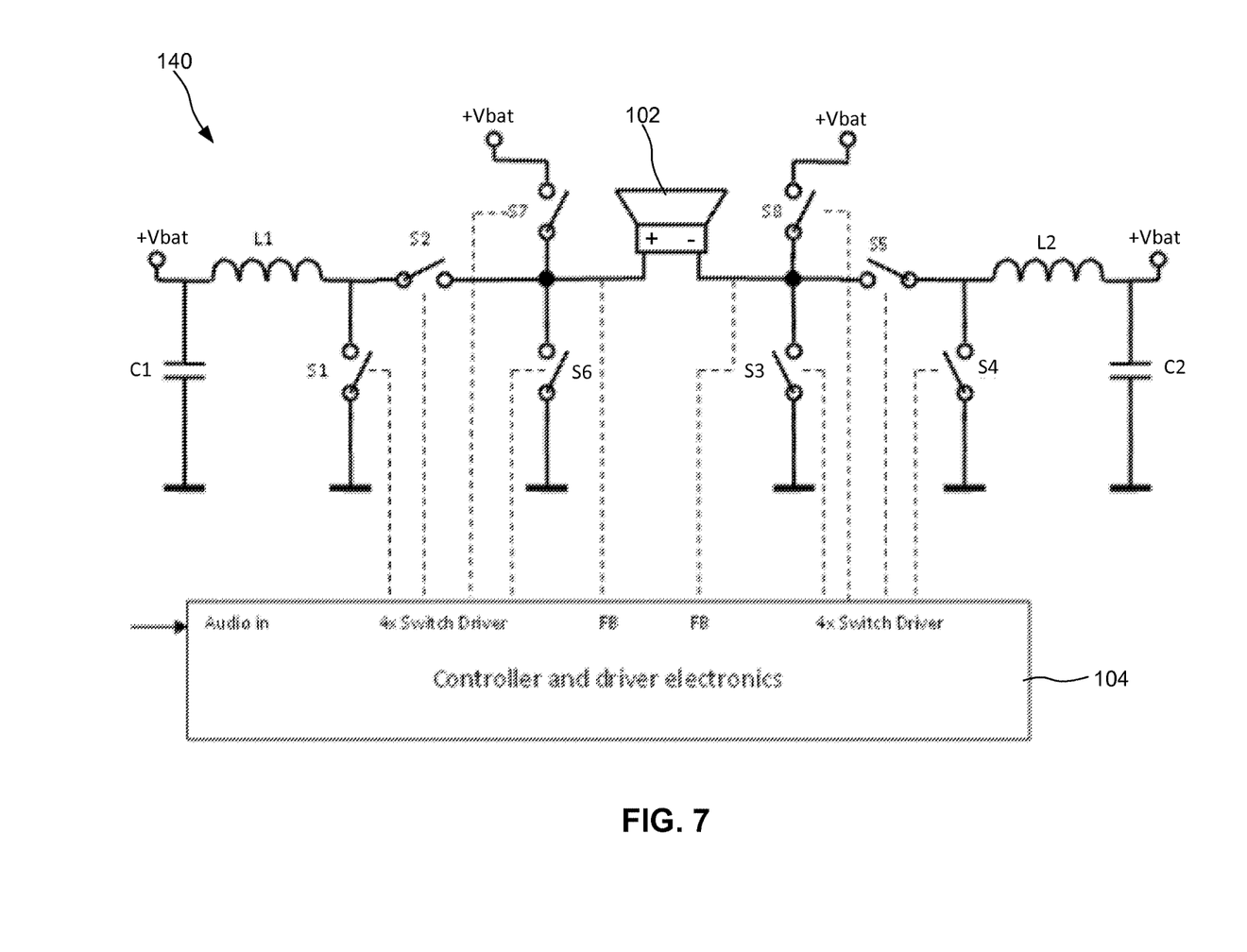
FIG. 7 is a circuit and block diagram of an output amplifier stage according to another embodiment of the present disclosure.

Referring now to FIG. 7, another example output amplifier stage 140 is shown, which is similar to the output stage 100 of FIG. 4. In addition, to the components of the output stage 100 described above, the output stage 140 of FIG. 7 further includes seventh switching circuitry S7 and eighth switching circuitry S8. More particularly, a first terminal of the seventh switching circuitry S7 is coupled to the power supply Vbat and a second terminal of the seventh switching circuitry is coupled to the load 102 (e.g., the positive terminal of the load). In addition, a first terminal of the eighth switching circuitry S8 is coupled to the power supply Vbat and a second terminal of the eighth switching circuitry is coupled to the load 102 (e.g., the negative terminal of the load). In another example, the first terminal of the eighth switching circuitry S8 may be coupled to a negative pole of the power supply —Vbat.

In FIG. 7, the third, sixth, seventh, and eighth switching circuitry S3, S6, S7, and S8 are configured as a class-D amplifier. More particularly, in use, the controller 104 actuates the switching circuitry S7 and S3 in a generally parallel relation, and also actuates the switching circuitry S6 and S8 in a generally parallel relation. Further, the controller 104 actuates the switching circuitry S7 and S8 in a generally inverse relation. The controller actuates the switching circuitry by alternatingly switching the circuitry pairs S7, S3, and S8, S6 on and off to provide an amplified representation of the audio signal 106 to the load 102.

As discussed above, in one example, the controller 104 is configured to switch between a first operating mode (or first operational settings) that uses one or more of the step-up driver stages of FIG. 4-7 for higher power requirements (e.g., higher than a predetermined threshold) and a second operating mode (or second operational settings) that uses the class-D amplifier for lower power requirements (e.g., lower than the predetermined threshold. The controller 104 may be configured to dynamically switch (e.g., without user input) between the first and second operating modes depending on whether an output level power requirement is higher or lower than the predetermined threshold, for example.

The controller 104 may implement the dynamic switching, for example, through control electronics in an ASIC and/or by using software or program instructions that are executable by the controller 104. In one example, the controller 104 may implement the dynamic switching in response to detecting a zero-crossing of the audio signal, and/or in response to detecting when the audio signal is as close to a zero-crossing as possible within a defined time from when a switching may be performed. In other examples, the controller 104 may control the switching using a moving average (e.g., a simple moving average or a moving average convergence/divergence filtering (MACD), peak detector, or similar technique.

The controller 104 may also use a trending estimation technique to control the switching. For instance, switching may be performed in response to determining that a predetermined number or threshold of peaks in the audio signal are over or under a predetermined level within a defined time. In another example, the controller 104 can analyze an average energy (e.g., mean) of the audio signal and peaks of the audio signal with a weighting factor between them to control the switching between the modes. In a further example, a transistor circuit may be added so that if the output voltage is high enough the transistor will open to allow the step-up driver stages to drive the output actuator.

Figure 8:
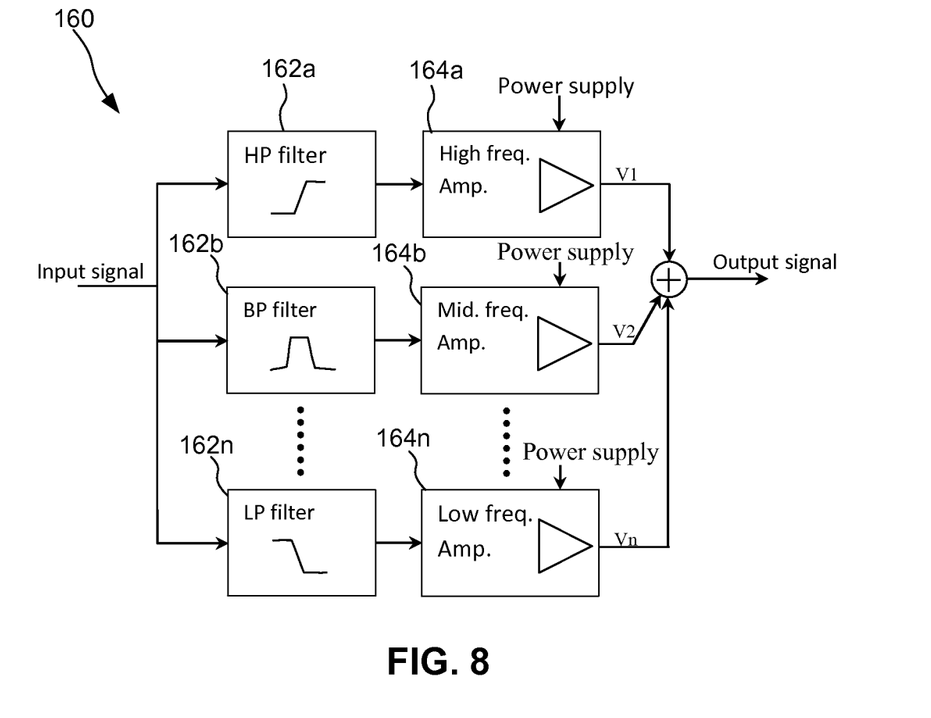
FIG. 8 is a circuit and block diagram illustrating an output amplifier stage according to another embodiment of the present disclosure.

Referring to FIG. 8, another example amplifier circuit or stage 160 is shown, which can form at least part of, or be used with, the other circuits described herein. In FIG. 8, the circuit 160 receives an input signal (e.g., encoded electronic signals that include audio data), and the input signal is provided to a set of two or more filter components 162a, 162b, 162n. The filter components filter the input signal into a set of two or more signal paths that correspond to different frequency bands or regions of the input signal. The filter components may include one or more different high-pass filters, band-pass filters, and/or low-pass filters. Cutoff or threshold frequencies between the different frequency bands can be adjusted as needed or desired. In one example, there are three filter components that filter the input signal into a frequencies below about 800 Hz, frequencies between about 800 Hz and about 4 kHz, and frequencies above about 4 kHz. Generally, there may be some overlap between the different filtered frequency components of the input signal.

In one example, the different signal paths of the input signal may be amplified differently depending on the nature of the coupled load (e.g., an actuator). An input signal that is configured for a high impedance actuator may be amplified using a relatively higher voltage and lower current, and an input signal that is configured for a low impedance actuator may be amplified using a relatively lower voltage and higher current.

In the circuit 160, the different signal paths are applied to amplifiers 164a, 164b, 164n, which amplify the different frequency components of the input signal and generate amplified signals V1, V2, Vn. The amplifiers may be coupled to different power sources for amplifying the respective input signal components. For instance, a relatively high voltage and relatively low current power source may be applied to the amplifier 164a, a relatively low voltage and relatively high current power source may be applied to the amplifier 164n, and a power source having a voltage and current between these relatively high and low values may be applied to the amplifier 164b. The power sources for the different amplifiers can be internally generated (as described in this disclosure), generated externally, or any combination thereof.

Generally, this configuration can help to avoid the frequency dependent power requirements of conventional hearing prostheses.

The amplified signals V1, V2, Vn may then be summed together or otherwise combined and applied as an output signal to a load (e.g., an actuator or transducer of the stimulation electronics 48). For an electromagnetic actuator the summing of the signals may be performed by a configuration of separate coils that are fed with separate signals. In this case, the summation is made in the magnetic field. For a piezoelectric actuator the summing of the signals may be performed by a configuration of separate piezoelectric devices that are mechanically connected to the output signal. In the case of a piezoelectric actuator, the summation is made in the mechanical domain.

Figure 9:
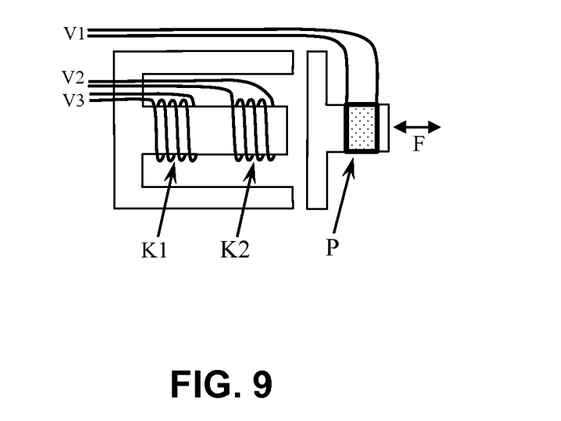
FIG. 9 is a circuit and block diagram of an actuator component according to an embodiment of the present disclosure.

FIG. 9 illustrates an example of an electromagnetic actuator with two coils K1, K2 together with one piezoelectric transducer P that are configured to work together to generate a mechanical alternating force F. Three signals V1, V2, and V3, which may correspond to the output signals V1, V2, Vn of FIG. 8, from three separate amplifier stages are provided to the circuit. The signal for the high frequency part V1 is provided to the piezoelectric transducer P, and the signals for the mid and low frequency parts V2 and V3 are provided to the actuator coils K1, K2. The number of piezoelectric transduces or actuator coils are not limited by the example shown in FIG. 9.

Figure 10:
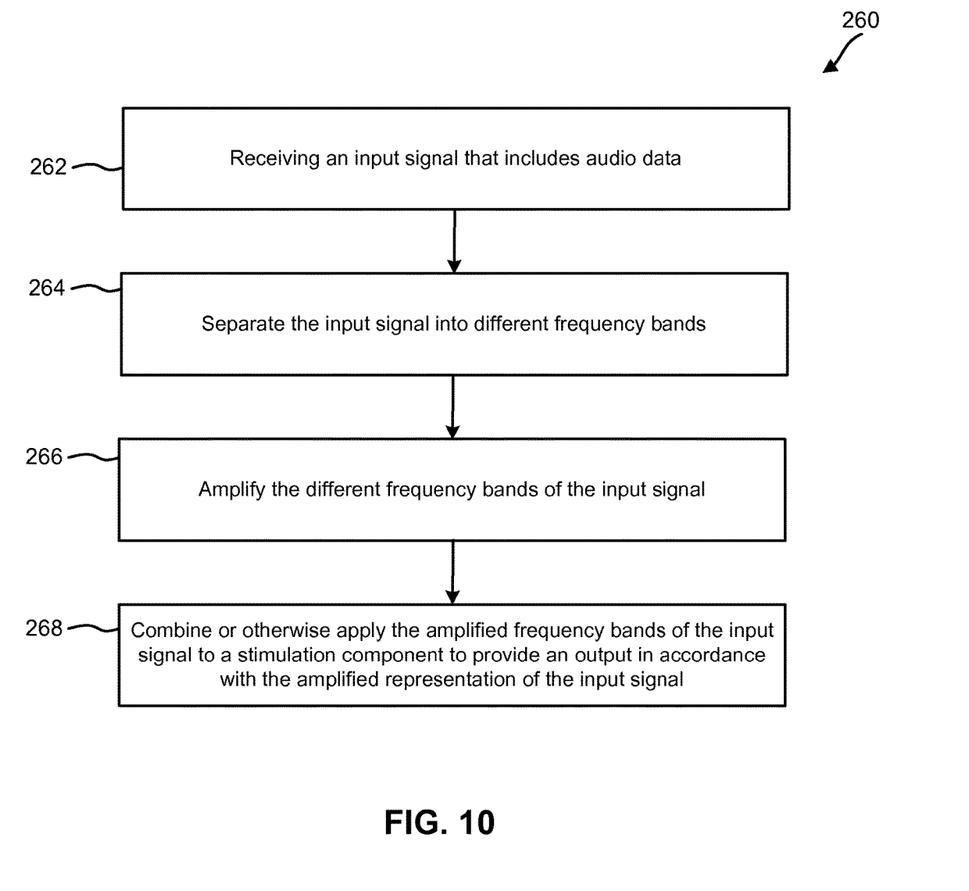
FIG. 10 is a flowchart showing a method for operating an output amplifier stage in accordance with an embodiment of the present disclosure.

Referring now to FIG. 10, one example method 260 is illustrated for operating the circuit 160 of FIG. 8. Generally, the method 260 may include one or more operations, functions, or actions as illustrated by one or more of blocks 262-268. Although the blocks 262268 are illustrated in sequential order, these blocks may also generally be performed concurrently and/or in a different order than illustrated. The method 260 may also include additional or fewer blocks, as needed or desired. For example, the various blocks 262-268 can be combined into fewer blocks, divided into additional blocks, and/or removed based upon a desired implementation.

In the method 260, at block 262, the circuit 160, for example, receives an input signal that includes audio data. At block 264, the circuit separates the input signal into different frequency bands as described hereinabove. At block 264, the circuit amplifies the different frequency bands of the input signal, as needed. Thereafter, at block 268, the amplified components of the input signal are combined or otherwise provided as an output signal to a stimulation component, for example.

In another example, the method 260 may also be implemented by the amplifier stage 140. For instance, the controller 104 may receive the input signal, and may then internally separate the input signal into different frequency bands. The controller 104 may then actuate the class-D amplifier in accordance with a low frequency band to generate an output signal to the load, and in parallel may actuate the step-up driver stages in accordance with a high frequency band to generate an output signal to the load.

Example Controller and Control Electronics

Figure 11:
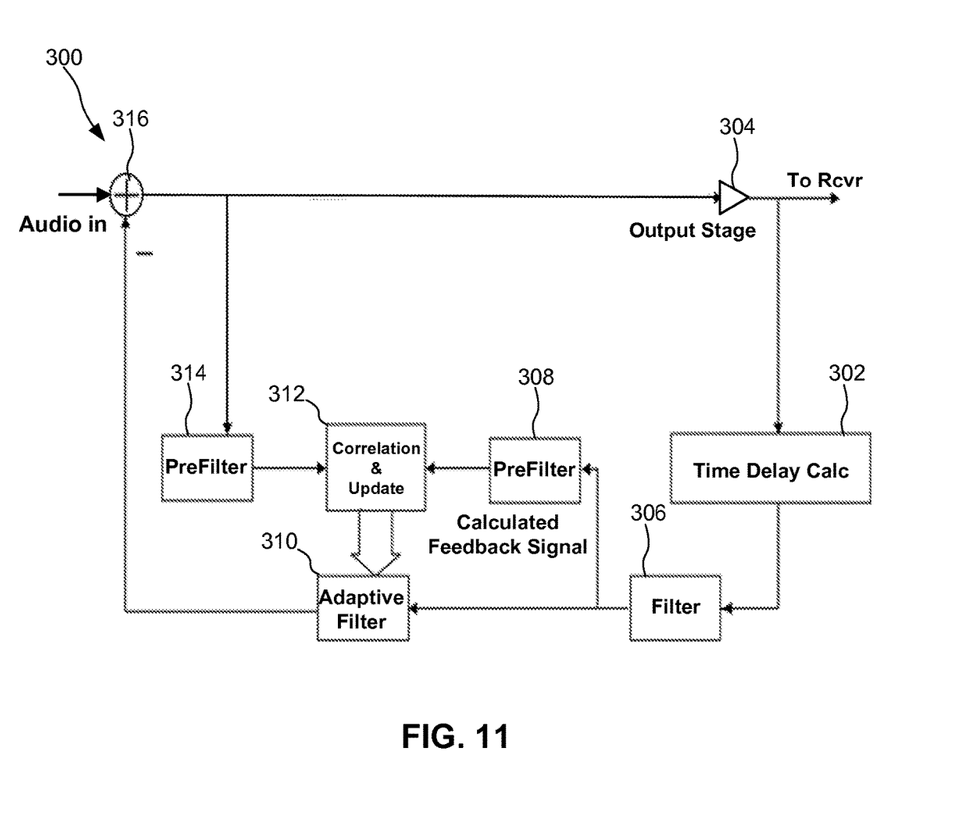
FIG. 11 is circuit and block diagram illustrating control circuitry according to an embodiment of the present disclosure.

FIG. 11 illustrates an example of control electronics 300, which may form part of the controller 104 and the filtering components 92 of FIG. 2, for example. Generally, the control electronics 300 may be configured to control (e.g., measure and compensate for) noise and other interference that may be caused by capacitive, resistive, and/or inductive components of the stimulation electronics and/or the output stage. In order to control the interference, the control electronics may include a feedback loop with the output stage, stimulation electronics, and an incoming audio signal or data. The control electronics may also include other filtering components and/or functions, such as signal conditioning that can be hard-coded in an ASIC and/or can be firmware based, and static filters and/or adaptive systems in the feedback loop to remove signal artifacts.

Generally, feedback loops may be used to remove ripple from a power supply voltage or clock jitter. In addition, control electronics may generally include "a modified sigma delta" converter for an incoming audio signal that uses compensation factors, such as from a lock-up table, feedback system, etc.

In an example that uses a lock-up table, the audio signal can be filtered by a pre-defined table of values or filter coefficients. These values or filter coefficients can be level and/or frequency dependent so that lower signal levels are shaped differently compared to higher signal levels. Such a filter can be set during the design and manufacture of the device or may be set or calibrated afterward, such as in the clinic during a fitting session. In one example calibration scenario, the device microphone can be used to analyze an audible output signal. Using the "recording" or audio data received from the microphone, the lock-up table can be created either by the device itself, by a portable computing device, or a stationary computer, for example. The resulting lock-up table filtering can include level compensation, phase modulation, and/or frequency modulation.

A feedback loop can also be used where the output signal is fed into a signal chain, or analyzed in parallel of the signal chain, and then used to create a filtering that is applied to the signal. The purpose of such a system is to compensate the signal for distortion and other interference created in the output stage.

Referring more particularly to the control electronics 300, in FIG. 11, a delay block 302 can add a relatively small delay to an output signal from an output stage 304 (such as the output stages described above), and a filter block 306 can apply filtering (e.g., low-pass filtering). An output from the filter block 306 is provided to a prefilter block 308 and to an adaptive filter block 310. The prefilter block 308 applies additional filtering and provides an output to a correlation and update block 312. The correlation and update block 312 also receives an input from another prefilter block 314. The prefilter block 314 applies filtering to an output from a mixer 316, which subtracts an output from the adaptive filter block 310 from the incoming audio signal. Generally, the correlation and update block 312 uses the outputs from the prefilter blocks 308, 314 to determine a correlation between the incoming audio signal and an amplified representation of the audio signal at an output of the output stage 304. The correlation and update block 312 provides an output that represents this correlation to the adaptive filter block 310. The adaptive filter block 310 uses the outputs from the filter block 306 and the correlation and update block 312 to apply adaptive filtering to the output from the filter block 306 and to provide an error feedback signal to the mixer 316, which subtracts the feedback signal from the incoming audio signal.

Example Output Stage

Figure 12:
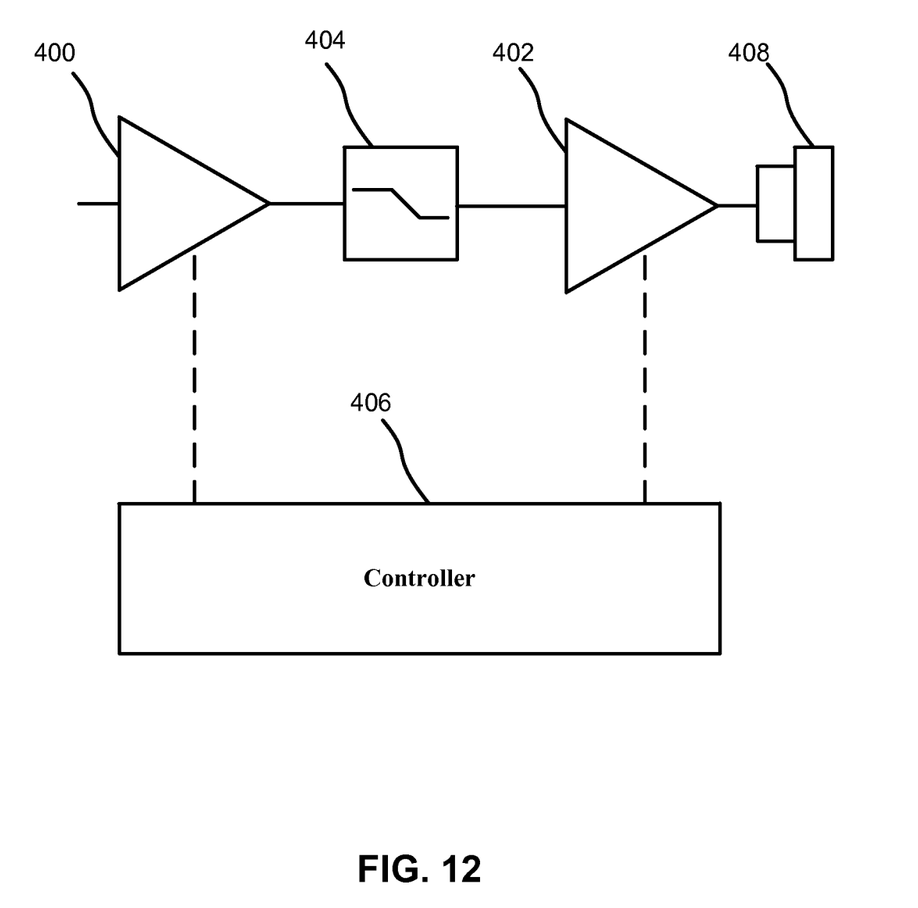
FIG. 12 is a circuit and block diagram of an output amplifier stage according to another embodiment of the present disclosure.

FIG. 12 illustrates another example output amplifier stage that includes a first amplifier 400 coupled in series with a second amplifier 402. The amplifiers 400, 402 may be coupled directly in series, although, in the present example, a filtering component 404 is coupled in series therebetween. In FIG. 12, the first and second amplifiers may be coupled to a controller or digital signal processor (DSP) 406, and stimulation electronics 408 may be coupled to receive an output signal from the second amplifier.

The first amplifier may be directly connected to the DSP 406 or incorporated therein. Further, the first amplifier may be configured to step-up a battery voltage and/or can be configured to provide an amplified electrical signal that includes audio data. In one example, the first and second amplifiers are both class-D amplifiers.

In one aspect, the DSP 406 is configured to limit a maximum output from the first amplifier for individual frequency bands, either directly or with a small time delay, in order to limit the amount of current being drained for the frequencies where the load impedance is low, as described above in the case of electromechanical stimulation components and piezoelectric actuators. In other words, the output level delivered from the first class-D amplifier to the second class-D is limited for the frequencies where the current drain otherwise would be too high for a power source to function properly. The DSP 406 may also be configured to limit the maximum output from the first amplifier depending on an operational mode. For instance, the DSP may lower the limitation of the output of the first amplifier when using wireless audio streaming, since a wireless audio streaming radio (e.g., the data interface/controller 26 or the communication electronics 32, 42) in this case will consume some current and, hence, only a lower output is allowed.

In another implementation, a power source (not shown) provides about 3.6-4.1 volts. In this example, the first class-D amplifier is combined with the DSP and is driven at 1.2 volts, and the second class-D amplifier is driven by 3.6 volts. In this implementation, the DSP is also used to limit the output for some of the frequencies (a discrete number of frequencies).

The filtering component 404, if included, may be a low pass filter to reduce switching frequency content, a relatively large resistor coupled in series to minimize bias voltage build-up over time, and/or a relatively large resistor coupled to ground to similarly minimize bias voltage build-up.

While various aspects and embodiments have been disclosed herein, other aspects and embodiments will be apparent to those skilled in the art. The various aspects and embodiments disclosed herein are for purposes of illustration and are not intended to be limiting, with the true scope being indicated by the following claims.

In one example, a hearing prosthesis circuit includes a first filter component configured to filter an input signal into a first signal path that corresponds to a first frequency band of the input signal. In this example, the circuit also includes a second filter component configured to filter the input signal into a second signal path that corresponds to a second frequency band of the input signal. Further, this example circuit also includes a first amplifier and a first power source coupled to the first amplifier, wherein the first amplifier is configured to utilize the first power source to generate a first amplified signal of the input signal in the first signal path. The example circuit also includes a second amplifier and a second power source coupled to the second amplifier, wherein the second amplifier is configured to utilize the second power source to generate a second amplified signal of the input signal in the second signal path. The first and second power sources may be different. In addition, the first and second amplified signals are configured to be applied to stimulation electronics.

What is claimed is:

1. A hearing prosthesis, comprising:
   at least one power source;
   at least one stimulation component;
   an output amplifier stage coupled between the at least one power source and the stimulation component, wherein the output amplifier stage is configured to operate in a first operating mode or a second operating mode,
   wherein in each of the first and second operating modes the output amplifier stage is configured to amplify an electrical signal that includes audio data and to provide the stimulation component with an amplified electrical signal enabling the at least one stimulation component to deliver stimulation to a recipient to evoke perception of the audio data; and
   a controller coupled to the output amplifier stage and configured to dynamically switch the output amplifier stage between the first and second operating modes,
   wherein amplification of the electrical signal is different in each of the first and second operating modes of the output amplifier stage.

2. The hearing prosthesis of claim 1, wherein the controller is configured to dynamically switch the output amplifier stage between the first and second operating modes based on a power output requirement associated with the at least one stimulation component.

3. The hearing prosthesis of claim 2, wherein the controller is configured to dynamically switch the output amplifier stage between the first and second operating modes depending on whether the power output requirement is higher or lower than a predetermined threshold.

4. The hearing prosthesis of claim 1, wherein the controller is configured to dynamically switch the output amplifier stage between the first and second operating modes based on one or more characteristics of the audio data.

5. The hearing prosthesis of claim 4, wherein the first operating mode is a music setting selected by the controller when the audio data includes music signals and the second operating mode is a phone setting selected by the controller when the audio data includes audio signals received from a phone.

6. The hearing prosthesis of claim 4, wherein the first operating mode is selected by the controller when the audio data corresponds with a noisy environmental classification and the second operating mode is selected by the controller when the audio data corresponds with a quiet environmental classification.

7. The hearing prosthesis of claim 4, wherein the controller is configured to dynamically switch the output amplifier stage between the first and second operating modes based on an amplitude of the audio data.

8. The hearing prosthesis of claim 1, wherein the first operating mode corresponds to a first hearing impairment and the second operating mode corresponds to a second hearing impairment, wherein the first hearing impairment is more severe than the second hearing impairment.

9. The hearing prosthesis of claim 1, wherein the output amplifier stage comprises first and second amplifiers, and wherein the controller is configured to use the first amplifier in the first operating mode to generate the amplified electrical signal or to use the second amplifier in the second operating mode to generate the amplified electrical signal, wherein the first amplifier provides greater amplification of the electrical signal than the second amplifier.

10. The hearing prosthesis of claim 9, wherein the first amplifier comprises a combined step-up converter and class-D amplifier, and wherein the second amplifier comprises a separate class-D amplifier.

11. The hearing prosthesis of claim 9, wherein the controller is configured to dynamically switch, at approximately a zero crossing of the electrical signal, between using the first amplifier or the second amplifier to generate the amplified electrical signal.

12. The hearing prosthesis of claim 1, wherein the output amplifier stage comprises at least first and second amplifiers that operate in parallel, wherein the first amplifier is configured to amplify portions of the electrical signal that are below a threshold frequency, and a second amplifier that is configured to amplify portions of the electrical signal that are above the threshold frequency.

13. The hearing prosthesis of claim 12, wherein the output amplifier stage comprises one or more filter components preceding the first and second amplifiers, and wherein the one or more filter components are configured to filter the electrical signal into different frequency portions.

14. A hearing prosthesis, comprising:
at least one power source;
at least one stimulation component;
an output amplifier stage coupled between the at least one power source and the stimulation component, wherein the output amplifier stage comprises first and second amplifiers selectively useable to generate an amplified electrical signal from an input signal that includes audio data; and
a controller dynamically operable in accordance with a first operational setting to use the first amplifier to generate the amplified electrical signal or operable in accordance with a second operational setting to use the second amplifier to generate the amplified electrical signal, wherein the first amplifier provides greater signal amplification of the electrical signal than the second amplifier.

15. The hearing prosthesis of claim 14, wherein the controller is configured to dynamically switch between the first and the second operational setting based on one or more characteristics of the audio data.

16. The hearing prosthesis of claim 15, wherein the first operational setting is a music setting and the second operational setting is a phone setting.

17. The hearing prosthesis of claim 15, wherein the first operational setting corresponds to a noisy environmental classification and the second operational setting corresponds to a quiet environmental classification.

18. The hearing prosthesis of claim 15, wherein the controller is configured to dynamically switch between the first operational setting and the second operational setting based on an amplitude of the audio data.

19. The hearing prosthesis of claim 14, wherein the first operational setting corresponds to a first hearing impairment and the second operational setting corresponds to a second hearing impairment, wherein the first hearing impairment is more severe than the second hearing impairment.

20. The hearing prosthesis of claim 14, wherein the first amplifier comprises a combined step-up converter and class-D amplifier, and wherein the second amplifier comprises a separate class-D amplifier.

21. The hearing prosthesis of claim 14, wherein the controller is configured to dynamically switch, at approximately a zero crossing of the input signal, between using the first amplifier or the second amplifier to generate the amplified electrical signal.

* * * * *